US011191578B2

(12) United States Patent
Najar

(10) Patent No.: US 11,191,578 B2
(45) Date of Patent: Dec. 7, 2021

(54) SPLIT STERNUM PROSTHESIS

(71) Applicant: SCANDINAVIAN REAL HEART AB, Västerås (SE)

(72) Inventor: Azad Najar, Västerås (SE)

(73) Assignee: SCANDINAVIAN REAL HEART AB, Vasteras (SE)

(*) Notice: Subject to any disclaimer, the term of this patent is extended or adjusted under 35 U.S.C. 154(b) by 0 days.

(21) Appl. No.: 16/074,983

(22) PCT Filed: Feb. 9, 2017

(86) PCT No.: PCT/EP2017/052850
§ 371 (c)(1),
(2) Date: Aug. 2, 2018

(87) PCT Pub. No.: WO2017/137488
PCT Pub. Date: Aug. 17, 2017

(65) Prior Publication Data
US 2019/0083151 A1 Mar. 21, 2019

(30) Foreign Application Priority Data

Feb. 10, 2016 (SE) .................................. 1650170-2
Jul. 21, 2016 (SE) .................................. 1651078-6

(51) Int. Cl.
A61B 17/80 (2006.01)
A61B 17/82 (2006.01)
A61B 17/04 (2006.01)

(52) U.S. Cl.
CPC ........ *A61B 17/8076* (2013.01); *A61B 17/823* (2013.01); *A61B 17/0466* (2013.01); *A61B 17/8061* (2013.01); *Y10S 606/905* (2013.01)

(58) Field of Classification Search
CPC ............. Y10S 606/905; A61B 17/8076; A61B 17/823; A61B 17/80; A61B 17/82;
(Continued)

(56) References Cited

U.S. PATENT DOCUMENTS 4,583,541 A 4/1986 Barry
8,425,572 B2* 4/2013 Grevious ........... A61B 17/8061
606/280
(Continued)

FOREIGN PATENT DOCUMENTS

EP 2823780 A1 1/2015
WO WO-2012/114360 A1 8/2012

OTHER PUBLICATIONS

International-Type Search Report dated Mar. 9, 2017 for ITS Request No. ITS/SE16/00217 for Swedish National Application No. 1651078-6, which was filed on Jul. 21, 2016 (Applicant—Scandinavian Real Heart AB) (4 pages).
(Continued)

*Primary Examiner* — Marcela I. Shirsat
(74) *Attorney, Agent, or Firm* — Ballard Spahr LLP

(57) ABSTRACT

The present disclosure relates to an implantable split sternum prosthesis to facilitate closure of the chest cavity and relieve pain after sternotomy operations. The split sternum prosthesis which after a surgical procedure is placed along the inline incision made in the sternum bone will also facilitate access to the chest cavity for patients in need of repeated surgical operations inside the chest cavity. The split sternum prosthesis comprises two elongated bone attachment plates, a first bone attachment plate and a second bone attachment plate. The first and he second bone attachment plates each have a bone attachment surface and a coupling surface. The first and second bone attachment plates are adapted be coupled together in a very close fit along their coupling surfaces.

20 Claims, 11 Drawing Sheets

(58) Field of Classification Search
CPC .............. A61B 17/842; A61B 17/8085; A61B 17/0466; A61B 17/683; A61B 17/8061; A61B 17/8047
USPC ......... 606/280, 71, 283, 284, 285, 286, 902, 606/915
See application file for complete search history.

(56) References Cited

U.S. PATENT DOCUMENTS

| | | | |
|---|---|---|---|
| 2007/0038218 A1 | 2/2007 | Grevious | |
| 2007/0055251 A1* | 3/2007 | Huebner | A61B 17/8047 606/279 |
| 2009/0234358 A1 | 9/2009 | Morales et al. | |
| 2011/0166612 A1* | 7/2011 | Bardaji Pascual | A61B 17/8076 606/86 R |
| 2014/0148863 A1* | 5/2014 | Barsoum | A61B 17/8076 606/319 |
| 2015/0045906 A1 | 2/2015 | Schumacher | |

OTHER PUBLICATIONS

International Search Report and Written Opinion dated May 16, 2017 by the International Searching Authority for Patent Application No. PCT/EP2017/052850, which was filed on Feb. 9, 2017 and published as WO 2017/137488 on Aug. 17, 2017 (Inventor—Azad Najar; Applicant—Scandinavian Real Heart AB) (12 pages).

International Preliminary Report on Patentability dated Feb. 1, 2018 by the International Searching Authority for Patent Application No. PCT/EP2017/052850, which was filed on Feb. 9, 2017 and published as WO 2017/137488 on Aug. 17, 2017 (Inventor—Azad Najar; Applicant—Scandinavian Real Heart AB) (38 pages).

* cited by examiner

SPLIT STERNUM PROSTHESIS

CROSS-REFERENCE TO RELATED APPLICATIONS

This application is a U.S. National Phase Application of International Application No. PCT/EP2017/052850, filed Feb. 9, 2017, which claims priority to Swedish Patent Application Nos. SE 1650170-2, filed Feb. 10, 2016, and SE 1651078-6, filed Jul. 21, 2016, each of which are hereby incorporated by reference in their entirety.

TECHNICAL FIELD

The present disclosure relates to an implantable split sternum prosthesis to facilitate closure of the chest cavity and relieve pain during recovery from sternotomy operations.

BACKGROUND OF THE INVENTION

A thoracotomy is an incision into the pleural space of the chest. It is performed by surgeons (or emergency physicians under certain circumstances) to gain access to the thoracic organs, most commonly the heart, the lungs, or the esophagus, or for access to the thoracic aorta or the anterior spine (the latter may be necessary to access tumors in the spine).

The first step performed during a thoracotomy is the median sternotomy in which a vertical inline incision is made along the sternum, after which the sternum itself is divided, or "cracked" into two parts. The rib cage may thereafter be pulled apart, thereby providing access to the heart and lungs for surgical procedures such as heart transplant, congenital heart defects or coronary artery bypass surgery. Thoracotomies are thought to be one of the most difficult surgical incisions to deal with post-operatively, because they are extremely painful and the pain can prevent the patient from breathing effectively, leading to atelectasis or pneumonia.

When the surgical procedure is finished, the cut sternum is pulled together by means of steel wires and allowed to heal. The healing process may take several months during which the patient may be in a lot of pain due to the rubbing of the cut sternum surfaces against each other with each movement of the chest wall during breathing.

Under certain circumstances the same patient may have to undergo thoracotomies more than once. For example patients who have received a heart prosthesis may have to undergo repeated openings of the chest in order to keep the heart prosthesis running smoothly.

Many efforts have been made during the last 50 years to develop a mechanical heart which can replace a diseased heart entirely. Until now only a few Total Artificial Hearts (TAH), i.e. mechanical hearts/heart prosthesis, have been developed which have the capacity to completely replace the diseased heart. A TAH differs from a heart assist, which only assists and supports a diseased part of the heart. This means that the heart assist prosthesis operates in parallel to the patient's own heart without the need to replace the heart which is the case of the total artificial heart. Numerous heart assist prostheses exist on the market either as left ventricular assist (LVAD), right ventricular assist devices (RVAD) or biventricular assist devices.

Although the technology in heart prostheses has improved immensely during the last decade, all heart prostheses still include many movable mechanical parts which tend to wear out and need to be replaced from time to time.

Once implanted inside the chest cavity there is no other way to service the heart prosthesis other than to repeat the thoracotomy and median sternotomy which again exposes the patient to all the potential complications as well as the pain associated with this strenuous surgical procedure. For this reason it would be advantageous to find a way to be able to rapidly open and close the chest in a manner which would cause minimal trauma for the patient.

It would also be an advantage if the cut surfaces of the sternum could be firmly stabilized during the healing process to prevent the movement of bone against bone and thereby reduce the pain for the patient during the period of recovery.

SUMMARY OF THE INVENTION

It is therefore an object to solve the above discussed problems by providing an implantable medical device as disclosed herein which improves the stability of the cut sternum bone during the rehabilitation process. A further advantage with the disclosed medical device is that it may facilitate for a patient to undergo thoracotomies, including repeated sternotomies, with minimal trauma. A solution to the before mentioned problems is a split sternum prosthesis which, after a sternotomy and the required surgical procedure, is placed along the inline incision made in the sternum bone during median sternotomy.

Median sternotomy is a type of surgical procedure in which a vertical inline incision is made along the sternum, after which the sternum itself is divided, or "cracked" into two halves. This procedure provides access to the heart and lungs for surgical procedures such as heart transplant, corrective surgery for congenital heart defects, or coronary artery bypass surgery.

The split sternum prosthesis comprises two elongated bone attachment plates, i.e. a first bone attachment plate and a second bone attachment plate. The first and the second bone attachment plates each have a bone attachment surface and a coupling surface. Each bone attachment surface is configured to be attached to incision surfaces formed along a vertical inline incision after a sternum has been subjected to median sternotomy and thereby divided into a first and second sternum half.

After the incision has been made along the median line of the sternum, and the sternum bone has been split into two halves, a first sternum half and a second sternum half, the two bone attachment plates are fitted to the two sternum halves. The bone attachment plates are fitted with their bone attachment surfaces facing the incision surfaces (i.e. the surfaces formed along the vertical inline incision) as well as to at least part of the anterior and posterior surfaces of the sternum halves respectively. This means that the first bone attachment plate is attached to the first sternum half and the second bone attachment plate is attached to the second sternum half.

The bone attachment plates advantageously have an extension in their longitudinal direction "x" that coincides with the length of the sternum bone and a transverse extension "y" in a direction substantially perpendicular to the longitudinal direction which corresponds to the tapering width of the sternum half from the incision line. The bone attachment plates also have an extension in the vertical direction "z" which equals the thickness of the sternum, said direction extending from the anterior to the posterior side of the sternum. Consequently each bone attachment plate covers the entire surface along the incision line and at least parts of the anterior and posterior surfaces of the respective sternum halves. In some instances the surface of the cut sternum bone may require trimming to adjust the fitting of a bone attachment plate thereto.

Alternatively the bone attachment plates may have a longitudinal extension which is shorter than the length of the sternum. In this embodiment the bone attachment surfaces only cover parts of the surfaces along the incision line, and instead two or more pairs of bone attachment plates are arranged along the surfaces of the incision line. The extension of the bone attachment plates in the longitudinal direction x is from 1.0-4.0 cm, preferably from 1.0-3.0 cm, more preferably from 1.0-2.0 cm.

Advantageously the bone attachment plates are made from a stiff material such as stainless steel or titanium. The bone attachment blades may also be made from a slightly pliable biocompatible material such as silicon.

Advantageously, before surgery the patient has undergone examinations and the sternum bone has been carefully measured to determine the shape such as length, width, thickness or any individual deviations to be able to customize the bone attachment plates to fit each individual patient.

Advantageously each bone attachment plate comprises an anterior section and a posterior section. The two sections may in some embodiments be provided as one piece, i.e. the anterior and posterior sections are manufactured as one piece to form a bone attachment plate, but advantageously they are provided as two separate parts that when fitted together form one bone attachment plate. Together the two sections cover at least parts of the surface along the incision line, but preferably the two sections cover the entire incision line surfaces. The two sections further cover at least parts of the anterior and posterior surfaces of each sternum half respectively. The provision of the bone attachment plate in two separate sections facilitates the fitting and fixation of the bone attachment plates to the two sternum halves.

The anterior and posterior sections of the bone attachment plates each have a longitudinal extension along at least parts of, but preferably along, the entire length of the sternum halves, i.e. from the clavicular bone to the proximal end of the xiphoid process. The anterior and posterior sections of the bone attachment plates each have a transverse extension that extends perpendicularly to the longitudinal extension from the incision line to at least half, but preferably across the whole width of the sternum half.

When the bone attachment plates are manufactured as one piece, each of the bone attachment plates has a first and a second section fold extending along the longitudinal extension x of said bone attachment plates separating each plate into an anterior section, a coupling surfaces and a posterior section. The anterior section having a first planar extension, said coupling surface having a second planar extension perpendicular to said first planar extension, and said posterior section having a third planar extension perpendicular to said second planar extension and parallel but opposite to said first planar extension. Said anterior and posterior sections are each provided with a bone attachment surface configured to be arranged to the anterior and posterior surfaces respectively of the sternum halves.

In embodiments when each of the bone attachment plates comprises separate anterior sections and posterior sections, the anterior sections s are arranged to the anterior sides of the sternum halves and the posterior sections of the bone attachment plates are arranged to the posterior sides of the sternum halves. Each of the anterior and the posterior sections have a section fold along their longitudinal extensions which divides said sections into a bone anchoring segment having a first planar extension and a coupling segment having a second planar extension, the first planar extension being arranged perpendicular to the second planar extension.

The bone anchoring segments of the anterior and posterior sections are configured to be arranged with their bone attachment surfaces facing the anterior and posterior surfaces respectively of the sternum halves. The bone attachment surfaces of the anterior and posterior coupling segments are configured to bear on the incision surfaces on each sternum half.

The anterior coupling segments extend along the z-direction from the longitudinally extending anterior section folds towards the posterior side of the sternum for a length that equals about half of the thickness of the sternum bone. The posterior coupling segments extend along the z-direction from the longitudinally extending posterior section folds towards the anterior side of the sternum for a length that equals about half the thickness of the sternum bone.

In embodiments wherein the anterior and posterior sections are formed as separate pieces, each of the coupling segments have a coupling segment edge extending in parallel with said section folds, wherein anterior and posterior coupling segment edges of each bone attachment plate are arranged to be coupled together in a tight fit to cover at least parts of, but preferably the entire first and second incision surfaces. This means that the anterior and posterior coupling segments are advantageously of a width such that anterior coupling segment edges meet posterior coupling segment edges and align edge to edge creating a tight interface along at least parts of, but preferably the entire incision surfaces of the sternum halves.

The bone attachment surfaces of the anterior and posterior sections may be smooth but advantageously the surfaces are rough with hills and valleys, or alternatively covered with netting. A rough surface enables the sternum bone to grow into the roughness of the bone attachment surface during the heeling process. If necessary, the incision surfaces may have to be trimmed to ensure a close fit to the bone attachment surfaces of the anterior and posterior sections.

The bone attachment plates are attached to the sternum halves by means of bone fastening means. Bone fastening means may be selected from the group consisting of bone cement, biocompatible glue, bone fixation screws, connector screws or bolts and nuts. The choice of bone fastening means depends on whether the bone attachment plates are expected to be removed in the future or not.

Preferably the bone fastening means are bolts and bolt receiving means as it may be disadvantageous to fasten bone screws into the bone itself. However in some embodiments the bone attachment plates may be fastened to the sternum halves by means of bone screws. Preferably the bolts, screws and/or bolt receiving means are made from stainless steel or titanium.

Advantageously, before fitting of the bone attachment plates each half of the sternum is provided with two or more bone through holes at varying distance from the median incision line. The bone through holes may be provided in a straight row along the incision or in a zig-zag pattern some distance from the incision. The number of bone through holes depends on the length of the sternum bone, but at least two bone through holes are required, preferably three, more preferably four or more bone through holes to ensure a tight fit of the bone attachment plates to the sternum halves.

Through bolts are used to fit the bone attachment plates to the sternum halves as it is more advantageous to not have to fasten screws into the bone directly. However in some embodiments the bone attachment plates may be screwed directly into the bone. Preferably the screws and through bolts are made from stainless steel or titanium.

The through bolts connect the anterior and posterior sections of the bone attachment plates to each one of the sternum halves. The posterior section of the bone attachment plate is advantageously arranged to the posterior side of the sternum half such that bolt receiving means located on the bone attachment surfaces of the posterior bone anchoring segments are aligned with and advantageously fitted into the bone through holes drilled in each of the sternum halves. The bolt receiving means may advantageously be nuts or cap nuts provided with internal threads, into which externally threaded through bolts may be fastened.

The anterior bone anchoring segments of the bone attachment plates are arranged with their bone attachment surfaces bearing onto the anterior sides of the sternum halves such that anterior section through holes provided on the anterior bone anchoring segments are aligned with the bone through holes provided on each of the sternum halves. The through holes in the anterior bone anchoring segments are advantageously counter sunk.

Through bolts are pushed into through holes provided on the anterior sections of the bone attachment plates and through the through holes in the sternum halves and are fastened into the bolt receiving means provided on the posterior sections of the bone attachment plates. The through bolts are tightened such that the bone attachment surfaces of both the anterior and posterior sections are arranged flush to the anterior and posterior sides, as well as to the incision surfaces of the cut sternum halves.

For practical reasons the through bolts are pushed through the sternum half from the anterior side of the sternum. However, it is possible that through bolts are pushed through the sternum half from the posterior side and fastened into bolt receiving means arranged on the bone facing side of the anterior section, but this procedure is more cumbersome.

The first and second bone attachment plates are configured be coupled together in a very close fit along their coupling surfaces. The coupling surfaces of the bone attachment plates are arranged to fit closely together when the chest is to be closed and the two sternum halves are pulled back together again. To ensure a very tight fit the coupling surfaces should preferably be smooth and flat. The two sternum halves are connected together by securing the first and second bone attachment plates together in a close fit by a closure arrangement.

It is important that the closure arrangement is secure and strong enough to withstand pulling forces and pressure from all different directions that may arise when the patient moves about. The closure arrangements must be easy to apply and remove to facilitate quick closing and opening of the chest cavity. Furthermore, it must be configured in a manner to not cause the patient any harm and minimum irritation when applied.

When the bone attachment plates comprise separate anterior and posterior sections the closure arrangement advantageously comprises anterior and posterior connecting means arranged on the first and second bone attachment plates which enable each one of the separate sections of the plates to be pulled together and joined in a tight fit by fastening means.

Advantageously the anterior and posterior connecting means arranged on the bone attachment plates comprise an overlapping feature. The anterior connecting means comprise first anterior projection means which protrude in a first lateral direction from the anterior section of the first bone attachment plate across the incision line to at least partly overlap into the anterior section of the second bone attachment plate when the two plates are connected. Said anterior connecting means further comprises second anterior projection means which protrude in a second lateral direction from the anterior section of the second bone attachment plate and opposite to the first lateral direction across the incision line to at least partly overlap into the anterior section of the first bone attachment plate when the two plates are connected. Cut-in portions are provided onto coupling surfaces of each first and second anterior section into which the first and second anterior projection means may protrude.

The first projection means may advantageously be lock loops arranged along the anterior section fold to project in a first lateral direction from the anterior anchoring segment of the first bone attachment plate to cover the anterior section fold and at least part of the anchoring segment of the second bone attachment plate. Advantageously cut-in portions are arranged on the coupling surfaces of the second bone attachment plate to receive said projecting lock loops.

The anterior section of the second attachment plate is provided with anterior section lock loops arranged along the longitudinal coupling segment edge of the anterior section on the second attachment plate projecting in a second lateral direction opposite to the first lateral direction, into cut-in portions provided on the anterior coupling surfaces of the anterior section on the first bone attachment plate.

The posterior sections of the bone attachment plates are provided with first and second posterior projection means. Said first posterior projection means protrude in a second lateral direction from the posterior section of the second bone attachment plate across the incision line to at least partly overlap into the posterior section of the first bone attachment plate. The posterior connecting means further include cut-in portions provided onto coupling surfaces of each first and second posterior section into which the posterior projection means may protrude.

The posterior projection means are advantageously posterior section lock loops arranged along the posterior longitudinal coupling segment edge and projecting in the lateral direction into posterior section cut-in portions provided on the posterior coupling segment on the first bone attachment plate.

The posterior section cut-in portions are provided with bolt closure receiving means arranged along the posterior section fold of the first bone attachment plate. Said bolt closure receiving means project in the lateral direction into cut-in portions provided on the posterior coupling segment on the second bone attachment plate.

The use of a split sternum prosthesis is especially advantageous in patients fitted with a heart prosthesis such as a heart assist or a total artificial heart (TAH).

Although technical advancements during the last decade have improved the durability and mechanical stability of heart prostheses, they still require service and replacement of mechanical parts such as motors, electronics, cogwheels and bearings from time to time.

The main advantage of using a split sternum prosthesis as described herein is that the patient in need of repeated sternotomies may be relieved from some of the trauma brought on by having to repeatedly cut the sternum and thereafter endure the painful recovery during the healing process.

When a patient fitted with the split sternum prosthesis as disclosed herein requires thoracotomy, the surgeon simply cuts the skin on the chest of the patient to reveal the sternum with the split sternum prosthesis. A quick opening of the chest cavity is facilitated by the use of through going closure bolts and anterior and posterior connecting means such as lock lops fitted to the first and second bone attachment plates. The through going closure bolts are unfastened from the bolt closure receiving means, removed from the lock loops and the chest cavity is opened. The patient does not have to endure the cumbersome procedure of cutting the sternum. Once the cavity is open the medical practitioner can perform the required procedure.

When the procedure is finished, the two sternum halves are drawn together by means of the anterior and posterior connecting means arranged on the first and second bone attachment plates. Thereafter the first and second bone attachment plates are locked into a secure and close fit using fastening means such as e.g. through going closure bolts and bolt closure receiving means. This procedure is much quicker than having to pull the two sternum halves together by means of steel wire.

Through the use of the split sternum prosthesis, the two sternum halves are firmly stabilized against each other by means of the tightly coupled bone attachment plates and any movement or rubbing of the cut sternum surfaces against each other is prevented. Thus, the patient fitted with a split sternum prosthesis is relieved of much of the pain normally associated with the recovery after a sternotomy.

Many accessories belong to the heart prosthesis such as implantable batteries, electronic control box, and energy transferring parts. Such accessories are in many cases, due to lack of the space inside the chest, often implanted inside the body at different locations such as for example in the abdomen. Implantation inside the abdomen may cause adverse side effects such as infections, inflammations and pressure symptoms. It is therefore advantageous if such accessories could be located in one place close to the chest to avoid long cables between the heart prosthesis and accessories.

In an embodiment the split sternum prosthesis comprises a sternal box for storing accessories to a heart prosthesis. The sternal box forms an integrated part of the split sternum prosthesis with its open end facing towards the anterior side of the patient. The inside of the sternal box is separated from the chest cavity by a metal plate which forms the posterior wall of the box. The sternal box is advantageously provided with a removable cover or lid which can easily be removed to reveal the heart prosthesis accessories placed therein. The cover or lid may be fastened to the sternal box by screws which can easily be removed. The junction between the sternal box and the lid is advantageously provided with a gasket to keep the inside of the box dry and free from body fluids.

Advantageously the posterior wall of the sternal box is provided with one or more junction holes through which cables from the accessories may run to reach the heart prosthesis in the chest cavity. The junction holes are preferably provided with gaskets to prevent body fluids from entering the sternal box.

By providing a sternal box integrated with the split sternum prosthesis the accessories required for the heart prosthesis are located very close to the heart thereby reducing the length of the cables between the prosthesis and the accessories. The accessories are easily reached without performing any advanced surgical procedures in the abdomen. Furthermore, adverse side effects such as infections, inflammations and pressure symptoms which may arise when the accessories are placed for instance in the abdominal cavity can be avoided by placing them in the sternal box instead.

In a further aspect the split sternum prosthesis may form a door through which a limited area of the chest cavity may be accessed without having to pull the sternum apart. Such a door may be useful during service of the heart prosthesis.

DETAILED DESCRIPTION

Figure 1:
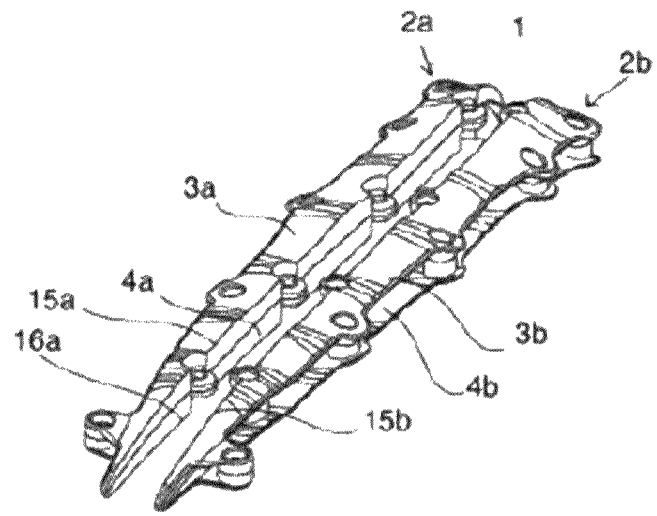
FIG. 1 is a view of the two bone attachment plates of the split sternum prosthesis

In the following detailed description, reference is made to the accompanying set of drawings that form a part of the description hereof and in which several specific embodiments are shown by way of illustration. It is to be understood that other embodiments are contemplated and may be made without departing from the scope or spirit of the present invention. The following detailed description, therefore, is not to be taken in a limiting sense.

Certain terms are used throughout the description and the claims that, while for the most part are well known, may require some explanation. It should be understood that, as used herein the term "posterior to the sternum" is intended to mean the side of the sternum facing the thoracic cavity. Thus the "posterior surface or side" of the sternum or sternum half is the surface or side of the sternum that normally faces the inside of the thoracic cavity. The term "anterior to the sternum" is intended to mean the side of the sternum which faces the skin on the front side of the patient's body.

The terms "a", "an", and "the" include plural referents unless the content clearly dictates otherwise.

The term "or" is generally employed in its sense including "and/or" unless the content clearly dictates otherwise The split sternum prosthesis 1 (FIG. 1) consist of two bone attachment plates, the first attachment plate 2a and the second attachment plate 2b. Each bone attachment plate 2a, 2b may consist of two or more interconnected sections as seen in FIGS. 1, 2, and 4-9 and 17-20, or alternatively the bone attachment plate 2a, 2b may be integral, i.e. manufactured as one piece as in seen in FIGS. 10-16 each plate. Advantageously the bone attachment plates 2a, 2b each comprise at least two sections, i.e. at least one anterior section 3a, 3b and at least one posterior section 4a, 4b which when connected together form a bone attachment plate 2a, 2b.

Hereinafter reference numbers denoting "a" refers to elements forming parts of the first bone attachment plate 2a and elements referred to as "b" form parts of the second bone attachment plate 2b. For instance the anterior section 3a and the posterior section 4a together form the first bone attachment plate 2a, and anterior section 3b and posterior section 4b together form the second bone attachment plate 2b (see FIG. 1).

Figure 3:
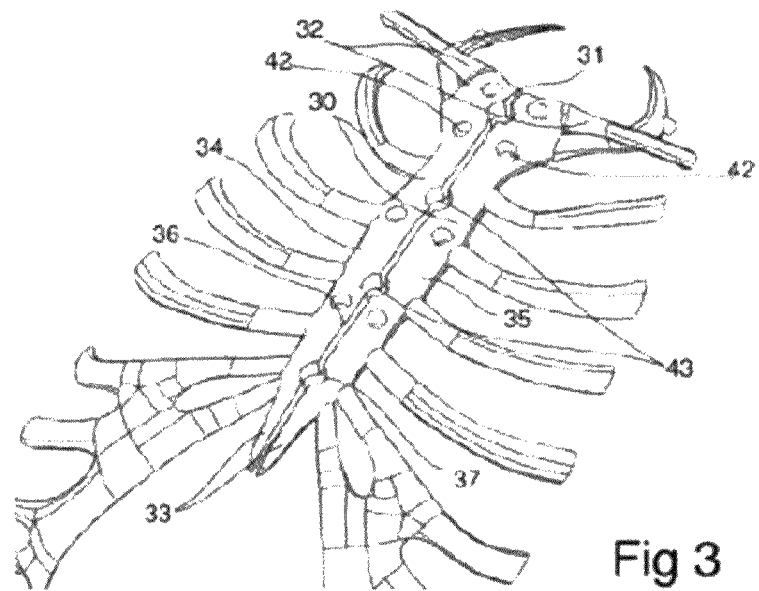
FIG. 3 is a view of the sternum bone after median incision and drilled bone and incision line through holes

During median sternotomy a vertical inline incision 31 is made along the sternum bone 30 extending from the clavicular bone 32 to the distal end of the xiphoid process 33 (see FIG. 3). Thereafter the sternum 30 itself is divided, or "cracked" into two halves, a first sternum half 34 and a second sternum half 35 forming a first incision surface 36 on the first sternum half 34 and a second incision surface 37 on the second sternum half 35.

Figure 2:
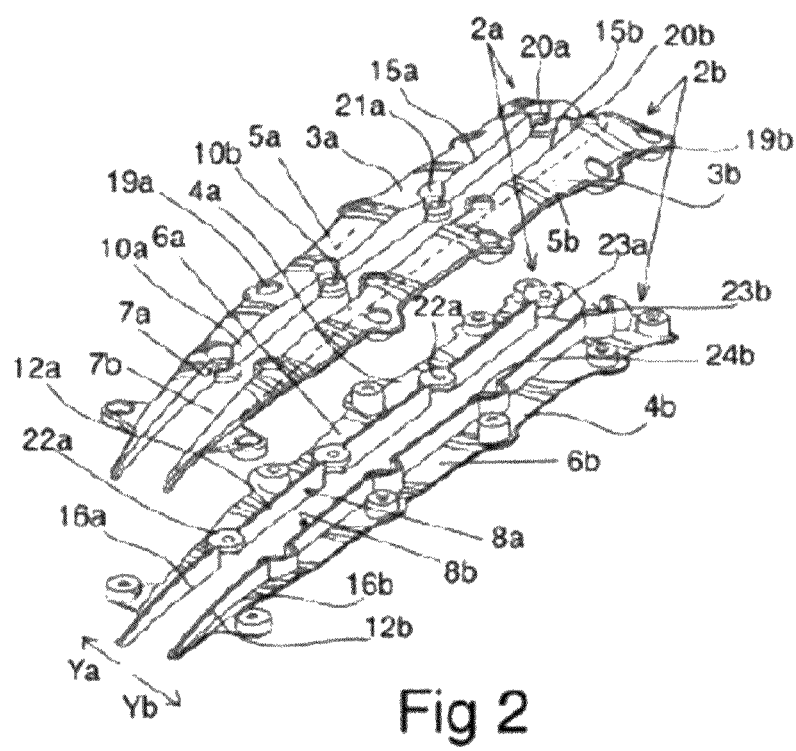
FIG. 2 is a view of the anterior and posterior sections of the bone attachment plates

The anterior sections 3 a, 3 b and the posterior sections 4 a, 4 b of the bone attachment plates 2 a, 2 b each have a bone attachment surface 5 a, 5 b, 6 a, 6 b and a coupling surface 7 a, 7 b, 8 a, 8 b (FIG. 2). Anterior bone attachment surfaces 5 a, 5 b are together with the posterior bone attachment surfaces 6 a, 6 b configured to cover the incision surfaces 36, 37 formed on each sternum half 34, 35 and at least part of the anterior and posterior surfaces 38, 39, 40, 41 of the sternum halves 34, 35. For example, with reference to FIGS. 6-7, anterior bone attachment surfaces 5 a, 5 b can comprise respective portions 90 a, 90 b that are configured to cover at least part of the anterior surfaces 38, 39 and respective portions 92 a, 92 b that are configured to cover at least a portion of the incision surfaces 36, 37 of the respective sternum halves 34, 35. Likewise, the posterior bone attachment surfaces 6 a, 6 b can comprise respective portions 94 a, 94 b that are configured to cover at least part of the respective posterior surfaces 40, 41, and respective portions 96 a, 96 b that are configured to cover at least a portion of the incision surfaces 36, 37 of the respective sternum halves 34, 35. Thus, the first and the second bone attachment plates 2a, 2b can each have at least one bone attachment surface 5a, 5b, 6a, 6b, and the at least one bone attachment surface of each of the first and second bone attachment plates can comprise a first portion (e.g., corresponding to portions 92a, 96a or portions 92b, 96b) that is configured to cover at least a portion of the incision surface of a respective sternum half 34, 35, a second portion (e.g., corresponding to portion 90a or portion 90b) that is configured to cover at least part of the anterior surface of the respective sternum half, and a third portion (e.g., corresponding to portion 94a or portion 94b) that is configured to cover at least part of the posterior surface of the respective sternum half.

The bone attachment plates 2a, 2b are advantageously made from a stiff biocompatible material like stainless steel, titanium or any other stiff biocompatible material. Each bone attachment plate 2a, 2b has a thickness of 1-5 mm, more preferably from 1-4 mm and more preferably 1-3 mm depending on the choice of material used to produce them.

Figure 4:
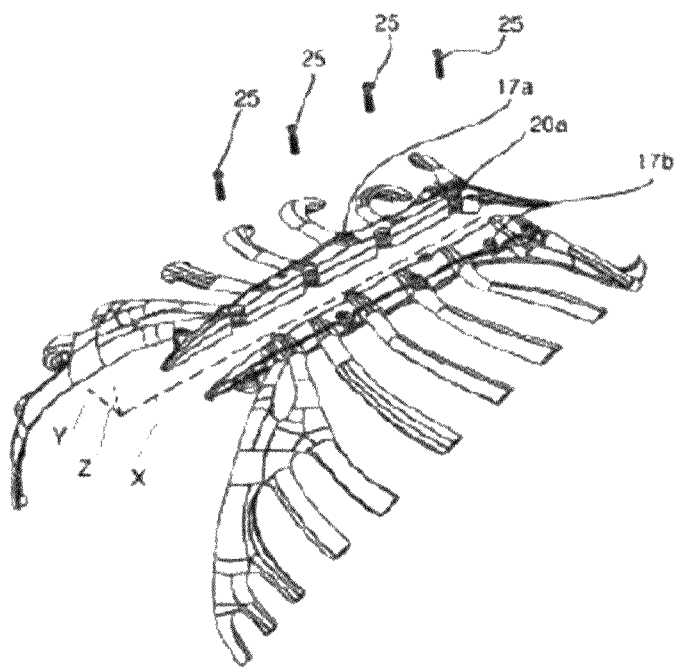
FIG. 4 is a view of the split sternum prosthesis arranged to the sternum.

The anterior 3a, 3b and posterior 4a, 4b sections of the bone attachment plates 2a, 2b are configured to be connected to the sternum halves 34, 35 formed during the median sternotomy. As seen in FIG. 4 the two bone attachment plates 2a, 2b have a longitudinal extension x in the x-direction, a transverse extension y (width) extending in the direction y that matches the sternum halves 34, 35. Furthermore the bone attachment plates have an extension in the z direction which corresponds to the thickness of the sternum. Advantageously the shape of the bone attachment plates 2a, 2b and/or the anterior 3a, 3b and posterior 4a, 4b sections have been carefully examined and shaped in advance to fit each patient individually.

The anterior 3a, 3b and posterior 4a, 4b sections respectively are each provided with a section fold 15a, 15b, 16a, 16b along their longitudinal extension. Said section folds 15a, 15b, 16a, 16b divide the anterior 3a, 3b and posterior 4a, 4b sections into bone anchoring segments 9a, 9b, 11a, 11b, and coupling segments 10a, 10b, 12a, 12b arranged perpendicular to each other (see FIGS. 1,2 and 6). The anterior 9a, 9b and posterior 11a, 11b bone anchoring segments have a width that coincides with the tapering width $y_a$, $y_b$ of the anterior sides 38, 39 and posterior sides 40, 41 of the sternum halves 34, 35 respectively. The anterior 10a, 10b and posterior 12a, 12b coupling segments, have a width that equals approximately half the thickness (i.e. half of the bone attachment plate extension in the z-direction) of the sternum bone 30 along the medial incision line 31 (see FIG. 5).

Figure 7:
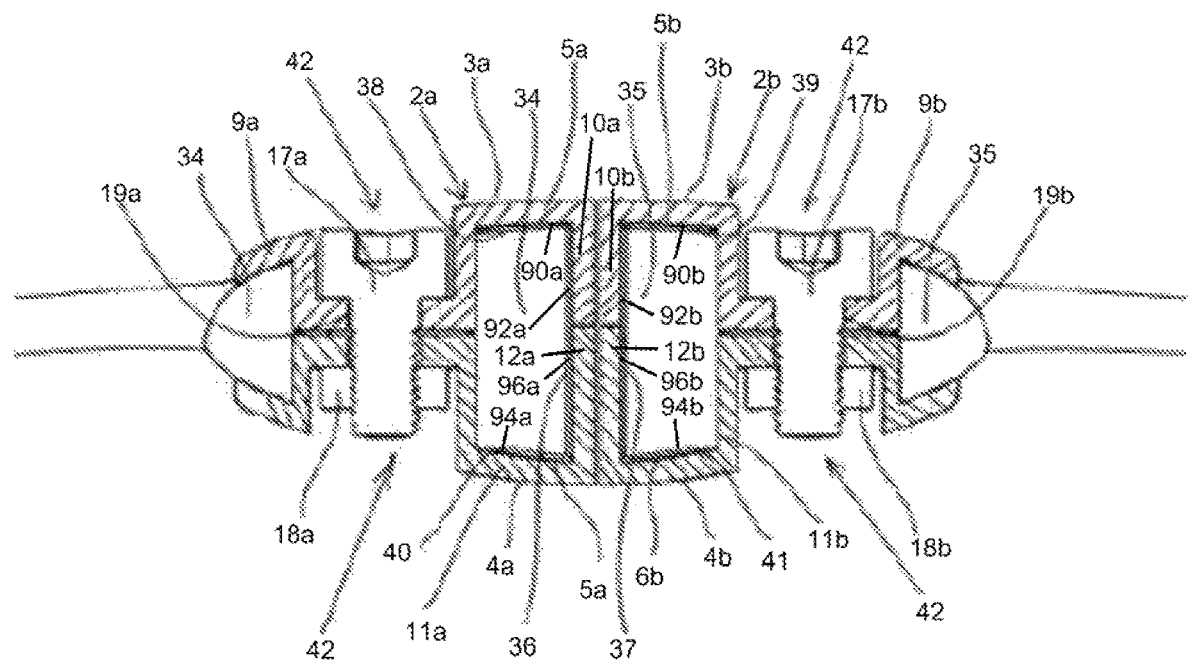
FIG. 7 is a cross-sectional view of the bone connecting means when arranged to the sternum halves

The anterior bone anchoring segments 9 a, 9 b of the bone attachment plates 2 a, 2 b are configured to be arranged with their bone attachment surfaces 5 a, 5 b facing the anterior surfaces of the sternum halves 38, 39. The longitudinal anterior section folds 15 a, 15 b of the anterior sections 3 a, 3 b are arranged along the median incision line 31 on the anterior sides 38, 39 of the first and second sternum halves 34, 35 with the anterior coupling segments 10 a, 10 b extending from the anterior section folds 15 a, 15 b in the z-direction towards the thoracic cavity to cover part of and preferably at least half of the incision surfaces 36, 37 on the sternum halves 34, 35 (see FIG. 5). As shown in FIGS. 2 and 7, the coupling segments 10 a, 10 b, 12 a, and 12 b can respectively define both the coupling surfaces 7 a, 7 b, 8 a, and 8 b as well as portions 92 a, 92 b and portions 96 a, 96 b of the bone attachment surfaces 5 a, 5 b, 6 a, 6 b.

Figure 5:
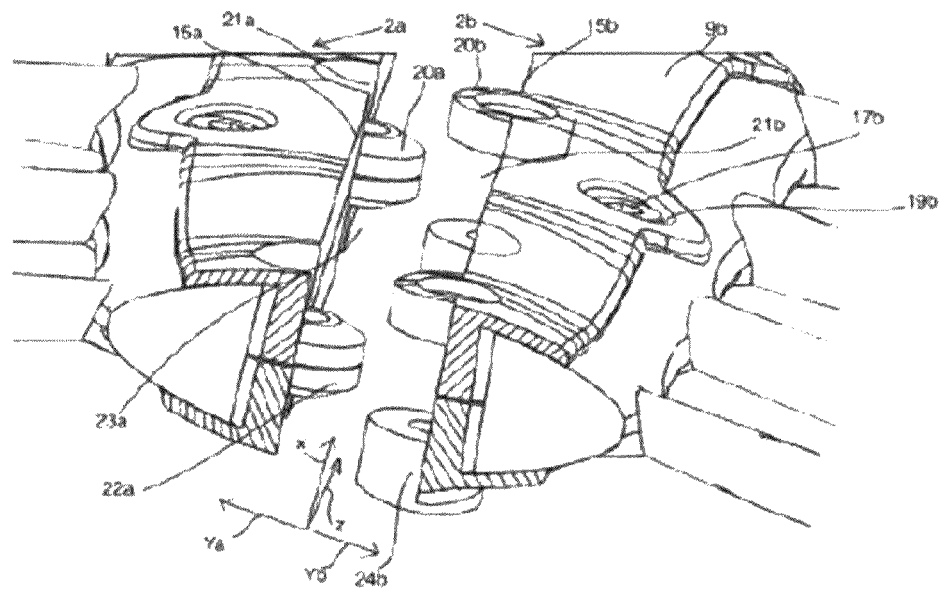
FIG. 5 is a detailed view of the bone attachment plates when arranged to the sternum halves and before closing
Figure 6:
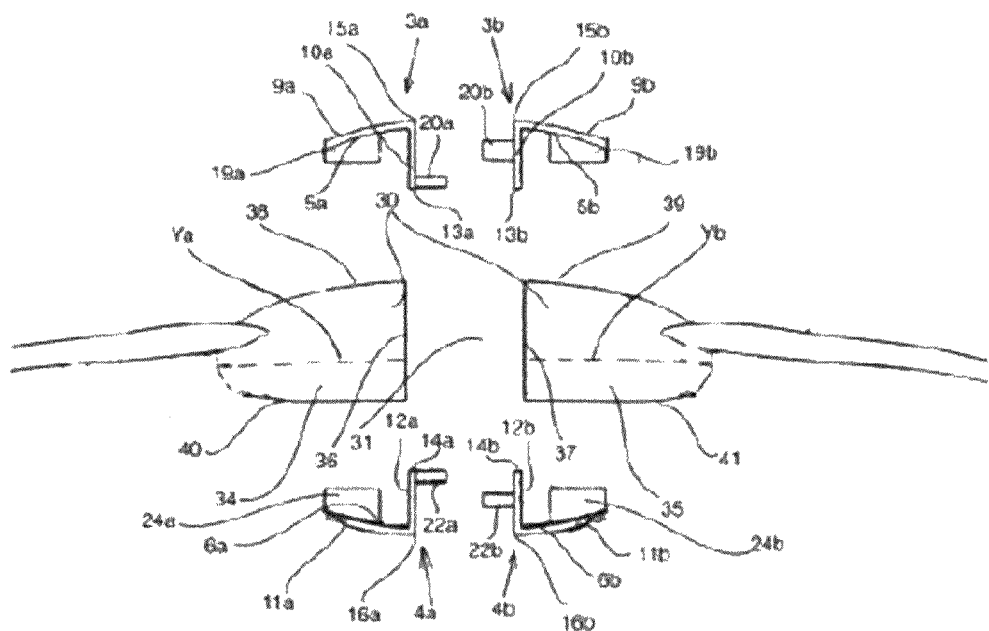
FIG. 6 is an exploded cross-sectional view of the bone attachment plates and the sternum halves.

The posterior bone anchoring segments 11a, 11b of the bone attachment plates 2a, 2b are configured to be arranged with their bone attachment surfaces 6a, 6b facing the posterior surfaces 40, 41 of the sternum halves (see FIGS. 6 and 7). The longitudinally extending posterior section folds 16a, 16b are arranged on the posterior sides 40, 41 of the two sternum halves 34, 35 on either sides of the median incision line 31 with the posterior coupling segment 12a, 12b extending from the posterior section folds 16a, 16b in the z-direction towards the anterior sides of the sternum halves 38, 39 to cover part of and preferably at least half of the incision surfaces 36, 37 on each of the sternum halves 34, 35 (see FIGS. 5 and 7).

The anterior and posterior coupling segments 10a, 10b, 12a, 12b each have a longitudinal coupling segment edge 13a, 13b, 14a, 14b distal to and parallel to the section folds 15a, 15b, 16a, 16b. The anterior and posterior longitudinal coupling segment edges 13a, 13b, 14a, 14b on the anterior 3a, 3b and posterior 4a, 4b sections are arranged to bear against each other in a tight fit to cover the entire first and second incision surfaces 36, 37 (see FIG. 7).

The bone attachment surfaces 5a, 5b, 6a, 6b of the anterior 3a, 3b and posterior 4a, 4b sections may be smooth but advantageously the surfaces 7a, 7b are rough with hills and valleys, or alternatively covered with netting (not shown). A rough surface enables the sternum bone 30 to grow into the roughness of the bone attachment surface 5a, 5b, 6a, 6b during the heeling process. If necessary, the incision surfaces 36, 37 may have to be trimmed to ensure a close fit to the bone attachment surfaces 5a, 5b, 6a, 6b of the anterior 3a, 3b and posterior 4a, 4b sections.

The bone attachment plates 2a, 2b are arranged to the sternum halves 34, 35 by means of bone fastening means. Bone fastening means may be of the group consisting of bone cement, biocompatible glue, bone fixation screws, connector screws or bolts and nuts.

The choice of bone fastening means depends on whether the bone attachment plates 2a, 2b are expected to be removed in the future or not. The bone attachment plates 2a, 2b may be fixed to the sternum halves 34, 35 by means of biocompatible glue, or bone cement if the split sternum prosthesis 1 is intended to permanently remain in place.

Preferably the bone fastening means are bolts 17a, 17b and bolt receiving means 18a 18b (see FIGS. 4, and 7) as it may be disadvantageous to fasten bone screws into the bone itself. However in some embodiments the bone attachment plates 2a, 2b may be fastened to the sternum halves 34, 35 by means of bone screws. Preferably the bolts, screws and/or bolt receiving means are made from stainless steel or titanium.

Before fitting of the bone attachment plates 2a, 2b, each sternum half 34, 35 is provided with two or more bone through holes 42 at varying distance from the incision line 31 (see FIG. 3). The bone through holes 42 may be provided in a straight row along the incision line 31 or in a zig-zag pattern (not shown) some distance from the incision line 31. The number of bone through holes 42 depends on the length of the sternum bone 30, but at least two bone through holes 42 are required, preferably three, more preferably four or more bone through holes 42 to ensure a tight fit of the bone attachment plates 2a, 2b to the sternum halves 34, 35.

In the embodiment disclosed in FIGS. 4 and 7 through bolts 17a, 17b and bolt receiving means 18a, 18b are used as bone fastening means to connect the anterior 3a, 3b and posterior 4a, 4b sections of the bone attachment plates 2a, 2b to the sternum halves 34, 35. The posterior sections 4a, 4b of the bone attachment plates 2a, 2b are fitted to the posterior sides 40, 41 of the sternum halves 34, 35 such that bolt receiving means 18a, 18b, arranged on the bone attachment surfaces 6a, 6b of the posterior bone anchoring segments 9a, 9b are aligned with and advantageously fitted into the bone through holes 42 drilled in the bone of sternum halves 34, 35. The bolt receiving means 18a, 18b may advantageously be e.g. nuts or cap nuts with internal threads, into which externally threaded through bolts 17a, 17b may be fastened.

The anterior sections 3a, 3b of the bone attachment plates 2a, 2b are fitted with their bone attachment surfaces 5a, 5b bearing on the anterior surface 38, 39 of the sternum halves 34, 35 such that anterior section through holes 19a, 19b provided on the anterior bone anchoring segments 9a, 9b are aligned with the bone through holes 42 on the sternum halves 34, 35. The anterior section through holes 19a, 19b are advantageously counter sunk (see FIG. 5) such that heads of the through bolts 17a, 17b will end up flush with the surfaces of the bone attachment plates 2a, 2b when arranged onto the sternum halves 34, 35.

Through bolts 17a, 17b are fitted into the anterior section through holes 19a, 19b of the anterior bone anchoring segments 9a, 9b and pushed through the bone through holes 42 in the sternum halves 34, 35 and fastened into the bolt receiving means 18a, 18b arranged on the posterior bone anchoring segments 11a, 11b (see FIG. 7).

The through bolts 17a, 17b are tightened such that the bone attachment surfaces 5a, 5b, 6a, 6b of both the anterior and posterior bone anchoring segments 9a, 9b, 11a, 11b are arranged flush to the anterior and posterior sides 38, 39 as well as to the incision surfaces 36, 37 of the each sternum half 34, 35 (see FIGS. 5 and 7). The advantage of using through bolts 17a, 17b and bolt receiving means 18a, 18b is that the bone attachment plates 2a, 2b are fastened in a very secure manner to the sternum halves 34, 35. This is absolutely necessary as strong forces are required to pull the two sternum halves 34, 35 together during closure of the chest cavity. With through bolts 17a, 17b arranged vertically through the sternum bone 30 and connected to bolt receiving means 18a, 18b on the opposite side of the sternum the pulling force during closure acts perpendicular to the direction of the through bolts.

For practical reasons the through bolts are fitted through the sternum halves from the anterior side of the sternum. However, it is possible that through bolts are pushed through the sternum halves from the posterior side and fastened to bolt receiving means arranged on the bone facing sides of the anterior sections, but this procedure is more cumbersome.

Figure 8:
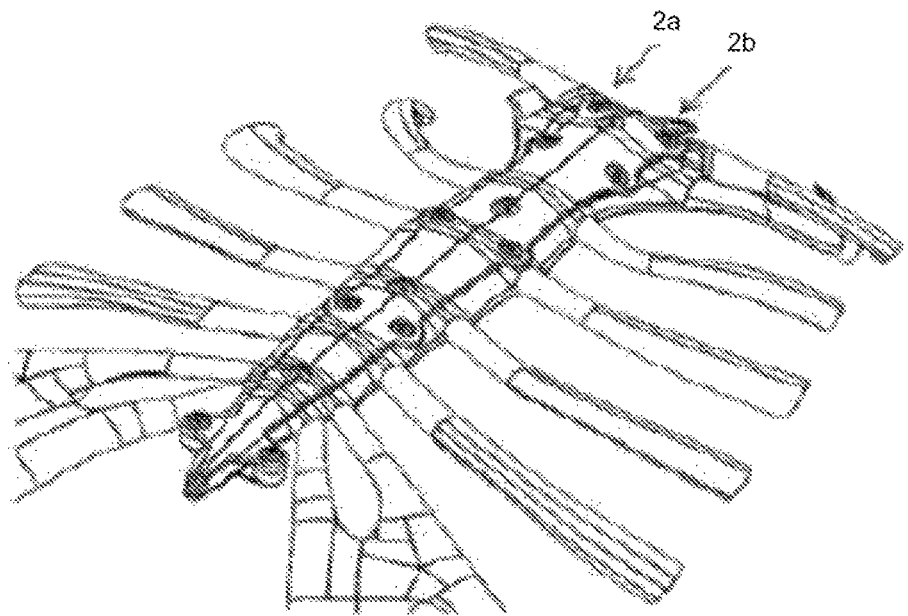
FIG. 8 is a perspective view of the split sternum prosthesis when fitted to the sternum and after closure
Figure 9:
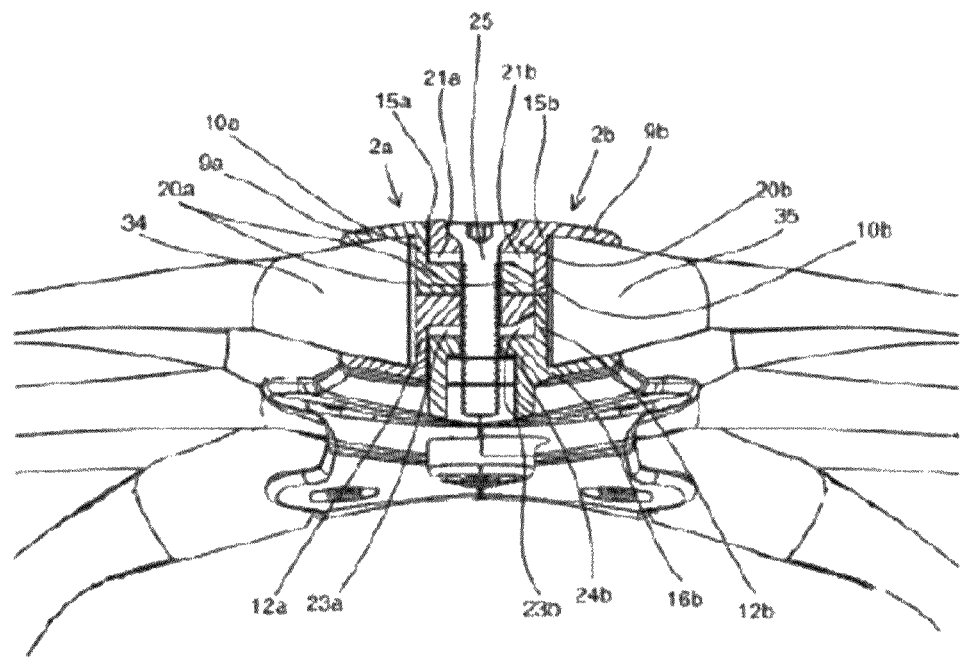
FIG. 9 is a cross-sectional view of the closure arrangement when fitted to the sternum halves
Figure 10:
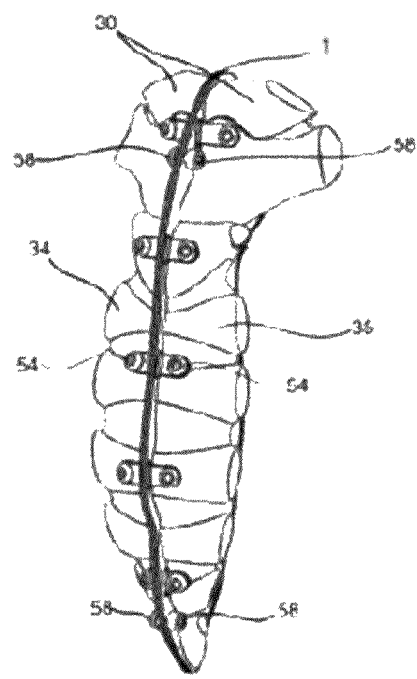
FIG. 10 is a view of an alternative embodiment of the closed split sternum prosthesis when fitted to a sternum bone

The split sternum prosthesis 1 further comprises a closure arrangement for pulling the two sternum halves 34, 35 together and locking them into a close fit when attached to the sternum (see FIGS. 8 and 9).

The closure arrangement comprises connecting means 20a, 20b, 22a, 22b arranged on the first and second bone attachment plates 2a, 2b which enable the plates 2a, 2b to be pulled together and joined in a tight fit by fastening means such as e.g. clamps, clips, braces, wires, screws and/or bolts. FIGS. 2, 4, 5, 6 and 9 disclose an advantageous closure arrangement wherein the connecting means comprise one or more anterior section lock loops 20b arranged along the anterior section fold 15b of the second bone attachment plate 2b. Said anterior section lock loops 20b project from the anterior section fold 15b in a first lateral direction $y_a$ and partially overlap onto the anterior section fold 15a and bone anchoring segment 9a of the second bone attachment plate 2a wherein anterior cut-in portions 21a are provided on the anterior coupling segment 10a of the second bone attachment plate 2a to receive said anterior section lock loops 20b (see FIGS. 2 and 5).

The anterior section 3a of the first attachment plate 2a is provided with anterior section lock loops 20a arranged along the longitudinal coupling segment edge 13a projecting therefrom in a second lateral direction $y_b$ from the cut-in portions 21a into cut-in portions 21b provided on the anterior coupling segment 10b of the second anterior section 3b. Said second lateral direction $y_b$ is opposite said first lateral direction $y_a$.

The closure arrangement further comprises posterior section lock loops 22a arranged along the posterior longitudinal coupling segment edge 14a of the first bone attachment plate 2a, and projecting in the lateral direction $y_b$ into posterior section cut-in portions 23b provided on the posterior coupling segment 12b on the second bone attachment plate 2b.

The posterior section cut-in portions 23b are provided with bolt closure receiving means 24b arranged along the posterior section fold 16b of the second bone attachment plate 2b. Said bolt closure receiving means 24b project in the lateral direction $y_a$ into cut-in portions 23a provided on the posterior coupling segment 12a on the first bone attachment plate 2a. Bolt closure receiving means 24b are advantageously cap nuts provided with an internal thread into which through going closure bolts provided with an external thread may be fastened.

Through holes 43 have been drilled along the incision line (see FIG. 3) which are large enough to accommodate the lock loops 20a, 20b, 22a, 22b and the bolt closure receiving means 24b. When the first and the second bone attachment plates 2a, 2b have been fitted to the first and second sternum halves 34, 35, the two plates 2a, 2b are pulled together such that the coupling surfaces 7a, 8a on the anterior and posterior coupling segments 10a, 12a of the first bone attachment plate 3, are brought into a tight closure with coupling surfaces 7b, 8b on the anterior and posterior coupling segments 10b, 12b of the second bone attachment plate 2b. The coupling surfaces 7a, 7b and 8a, 8b should be smooth and preferably flat to ensure a very tight fit (see FIGS. 5, 7 and 9).

Through going closure bolts 25 are fitted into and pushed through the anterior lock loops 20b of the second bone attachment plate 2b, through the anterior lock loops 20a of the first bone attachment plate 2a, through the posterior lock loops 22a of the first bone attachment plate 2a and thereafter secured into the bolt closure receiving means 24b arranged on the second attachment plate 2b (see FIG. 9).

The closure arrangement described above provides an effective closure of the chest cavity wherein each one of the anterior and posterior sections 3a, 3b, 4a, 4b are secured to each other in a double shear bolt connection wherein the pulling forces from all sections 3a, 3b, 4a, 4b are evenly distributed along the through going closure bolt 25.

In an alternative embodiment the split sternum prosthesis 1 (FIG. 10) consist of two bone attachment plates, the first attachment plate 50a and the second attachment plate 50b. In this embodiment each bone attachment plate 50a, 50b comprises three segments; an anterior segment 53a, 53b, a coupling segment 54a, 54b and a posterior segment 55a, 55b, but the three sections are manufactured as one piece. Each one of the bone attachment plates 50a, 50b is connected to the first and second sternum half 34, 35 respectively by means of bone fastening means 54a, 54b. The bone fastening means are in this embodiment at least two bone fixture screws 54a, 54b, preferably three or more bone fixture screws (see FIG. 12). The fixture screws 54a, 54b are advantageously made from stainless steel or titanium.

Other biocompatible materials such as glue, bone cement can be used alone or together with the fixture screws 54a, 54b to fix the prosthesis to the sternum halves 34, 35. Each bone attachment plate 50a, 50b, is designed to anatomically fit the curvature of the sternum 30.

Figure 11A:
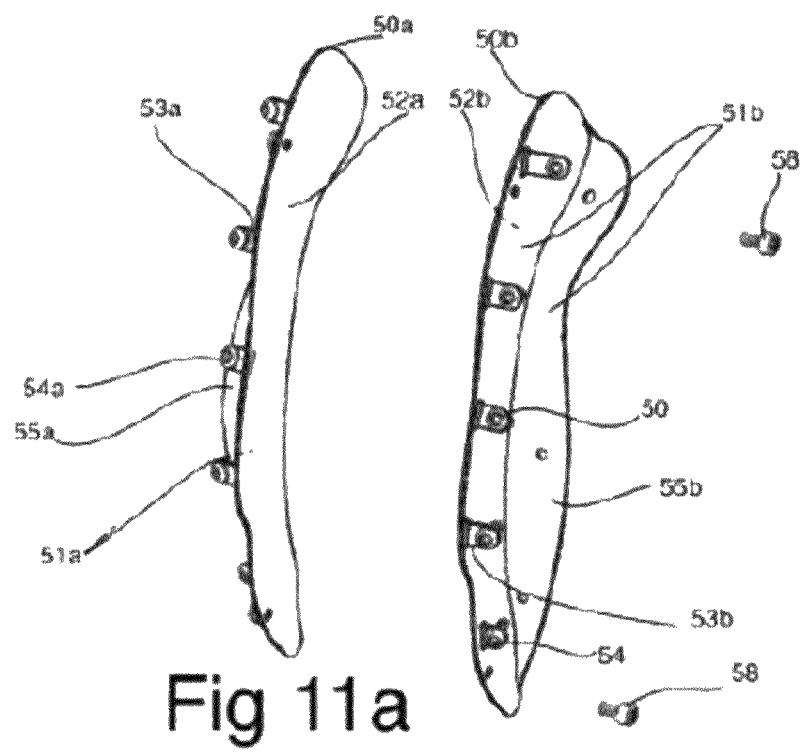
FIG. 11a is a view of the two attachment plates of one alternative embodiment of the split sternum prosthesis
Figure 11B:
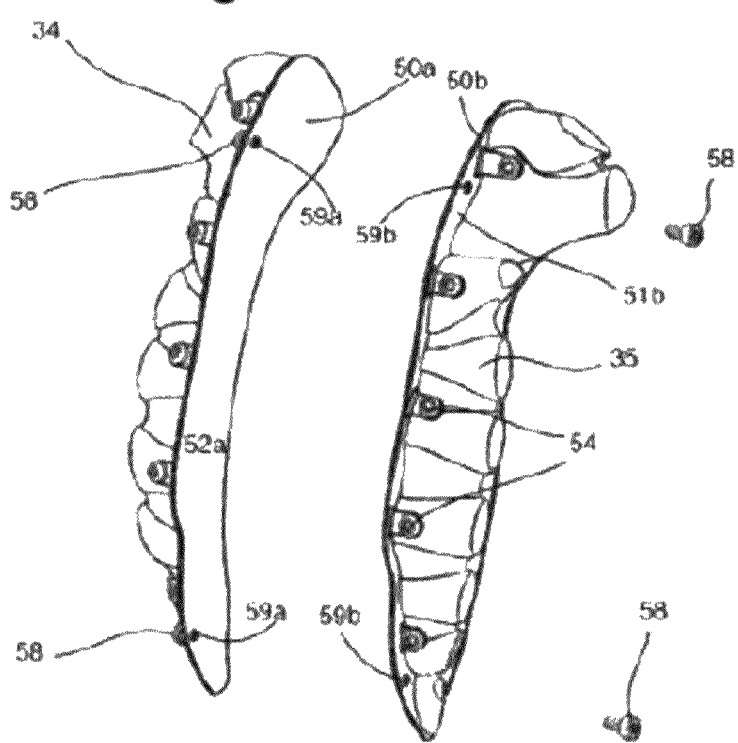
FIG. 11b is a view of the two attachment plates of one alternative embodiment of the split sternum prosthesis when fitted to the two sternum halves

Each bone attachment plate 50a, 50b has two surfaces, a bone attachment surface 51a, 51b, and a coupling surface 52a, 52b FIGS. 11a and 11b). The bone attachment surfaces 51a, 51b may be smooth but advantageously the surfaces are rough with hills and valleys or covered with netting. The coupling surfaces 52a, 52b should be smooth and preferably flat. Each bone attachment plate 5a, 50b is 1-5 mm thick preferably 1-4 mm, more preferably 1-3 mm thick depending on the choice of material used to produce them.

The length of the bone attachment plates 50a, 50b in the longitudinal direction x should advantageously be substantially the same as the length of the sternum 30 but the width of each bone attachment plate 50a, 50b in the direction y, i.e. transverse to the longitudinal direction x can vary. Each of the bone attachment plates 50a, 50b has a first and a second section fold 56a, 56b, 57a, 57b, extending along the longitudinal extension x of said bone attachment plates 50a, 50b separating said bone attachment plates 50a, 50b into the anterior segment 53a, 53b, the coupling surfaces 52a, 52b and the posterior segment 55a, 55b, said anterior segment 53a, 53b having a first planar extension, said coupling surface 52a, 52b having a second planar extension perpendicular to said first planar extension, and said posterior section 55a, 55b having a third planar extension perpendicular to said second planar extension and parallel but opposite to said first planar extension.

Figure 12:
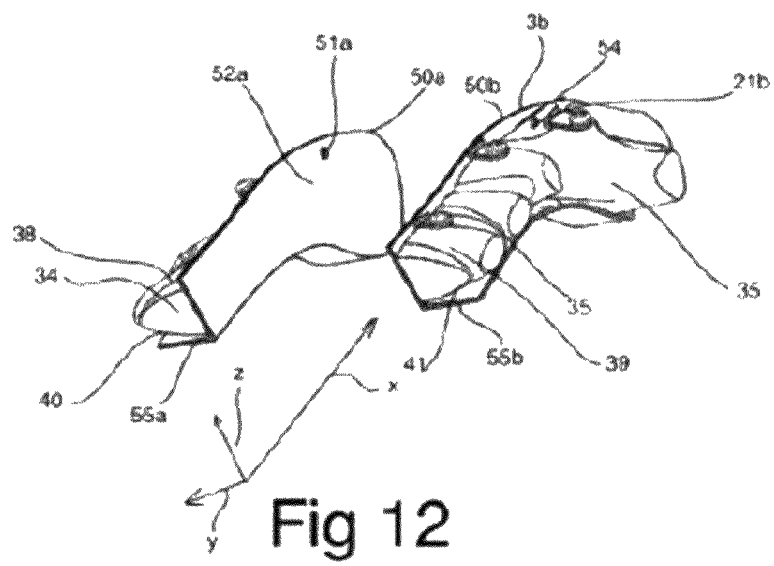
FIG. 12 is a perspective view of the one alternative embodiment of the split sternum prosthesis when fitted to a sternum bone before closing

In some embodiments there is only a slight overlap of the anterior segments 53a, 53b of the bone attachment plates 50a, 50b onto the anterior sides 38, 39 of the sternum halves 34, 35 (see FIGS. 12 and 13) and the posterior segments 55a, 55b of the bone attachment plates 50a, 50b cover substantially the entire posterior surfaces 40, 41 of the sternum halves 34, 35 (see FIG. 12).

The anterior segments 53a, 53b of the bone attachment plates 50a, 50b may be attached to the anterior surfaces 38, 39 of the sternum halves 34, 35 by means of bone fastening means 54a, 54b such as e.g. bone fixture screws The posterior segments 55a, 55b of the bone attachment plates 50a, 50b may be fastened to the posterior surfaces 40, 41 of the sternum by means of bone fastening means such as e.g. bone fixture screws (not shown).

The coupling surfaces 52a, 52b of the two bone attachment plates 50a, 50b are advantageously flat and smooth such that when the bone attachment plates 50a, 50b are pulled towards each other to close the chest cavity the coupling surfaces 52a, 52b fit firmly against each other in a tight fit.

Figure 13:
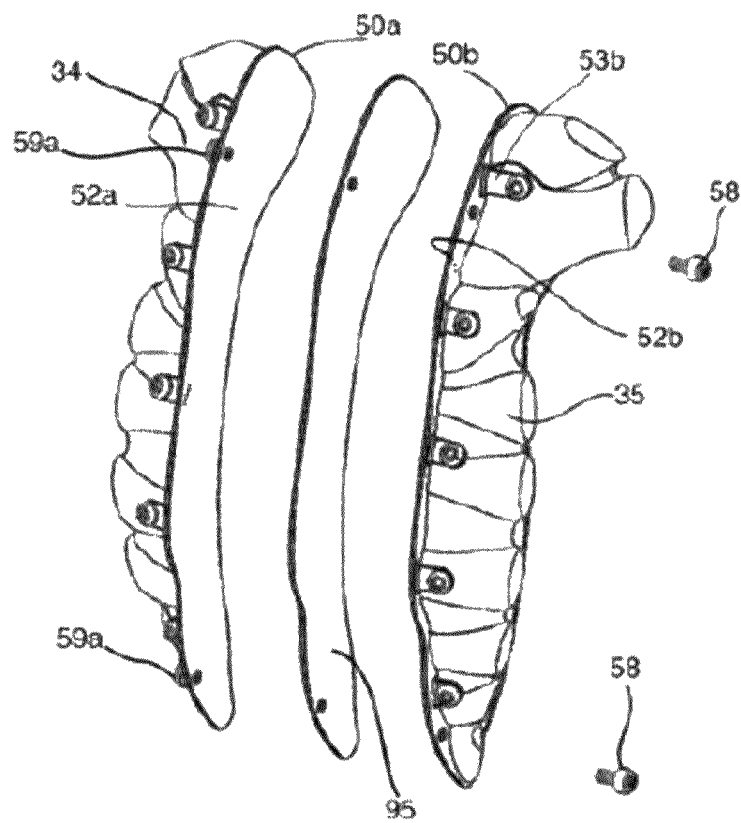
FIG. 13 is a view of one alternative embodiment of the split sternum prosthesis including sealing means fitted to a sternum bone before closing.

The bone attachment plates 50a, 50b are brought together in a tight fit by means of a closure arrangement. As seen in FIGS. 11, 12 and 13 the closure arrangement is through holes 59a, 59b drilled in the anterior section upper edge through which through bolts 58 are fitted. The through bolts 58 are advantageously fastened into nuts (not shown) to enable the two bone attachment plates to be pulled together in a tight fit. 1.

Advantageously there is a leak protection layer 95 (FIG. 13) assembled between two coupling surfaces 52a, 52b of the bone attachment plates 50a, 50b to create a leak proof connection said plates 50a, 50b. The thin leak protection layer 95 is preferably made of silicone, polyurethane or any other soft and compressible biocompatible material. Advantageously the leak protection layer 95 is coated and/or treated with an antiseptic substance to prevent migration of bacteria from the subcutaneous area between the bone attachment plates 50*a*, 50*b* to the inside of the chest cavity during healing of the skin after surgery in case any infections arise during the skin healing process.

Figure 14:
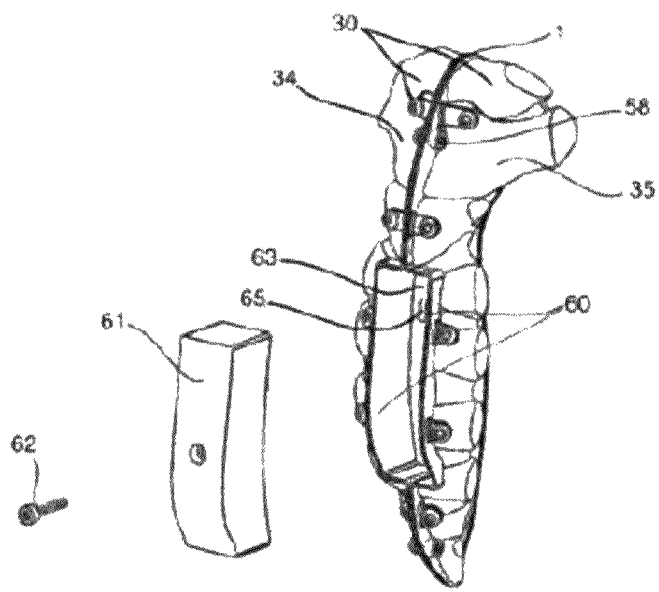
FIG. 14 is view of one alternative embodiment of the split sternum prosthesis including an accessories box fitted to a sternum bone before closing of the sternum box.
Figure 15:
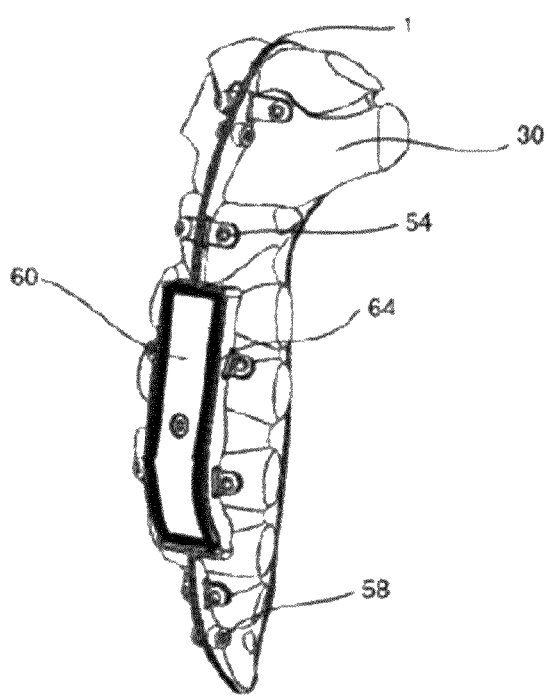
FIG. 15 is view of one alternative embodiment of the split sternum prosthesis including an accessories box provided with a sealing means.
Figure 16:
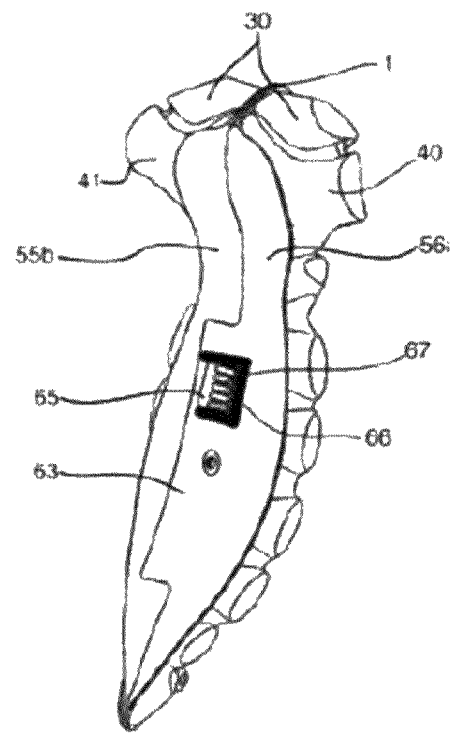
FIG. 16 is a view of one alternative embodiment of the split sternum prosthesis including an accessories box fitted to a sternum bone as viewed from inside the thoracic cage

FIGS. 14, 15 and 16 disclose a split sternum prosthesis 1 provided with a sternum box 60. The sternum box 60 forms an integrated part of the split sternum prosthesis 1 and fits in the center of the sternum bone 30. To make room for the sternum box, parts of the sternum bone 30 is removed to accommodate the sternum box 60. The sternum box 60 is made of the same material as the split sternum prosthesis 1.

The sternum box 60 is covered by a box cover 61 (FIG. 14) which may advantageously be designed to contain accessories for a heart prosthesis such as batteries and electronic control circuitry to control the heart prosthesis. The electronics and batteries can thereby easily be replaced if damaged or the batteries have worn out. The box cover 61 may easily be assembled to or disassembled from the sternal box 60 by a box fastening means such as a box screw 62.

The bottom wall 63 of the sternum box 60 is made from metal and separates the inside of the sternum box 60 from the chest cavity. Advantageously the sternum box 60 is made leak proof by arranging a biocompatible gasket 64 at the rim of the sternum box 60 or alternatively the inside of the box cover 61 is provided with a gasket to prevent body fluids from entering the sternal box 60 (see FIG. 15).

The bottom wall 63 of the sternum box 60 is provided with one or more junction holes 65 (FIG. 16) through which cables to and from the heart prosthesis may pass. Each hole is made leak proof by sealing gaskets 66 around the opening. The bottom wall may also be fitted with e.g. one or more electrical connector plugs 67 to facilitate the electrical connections between the heart prosthesis (not shown in figures) and the electronics in the cover box 61.

Figure 17:
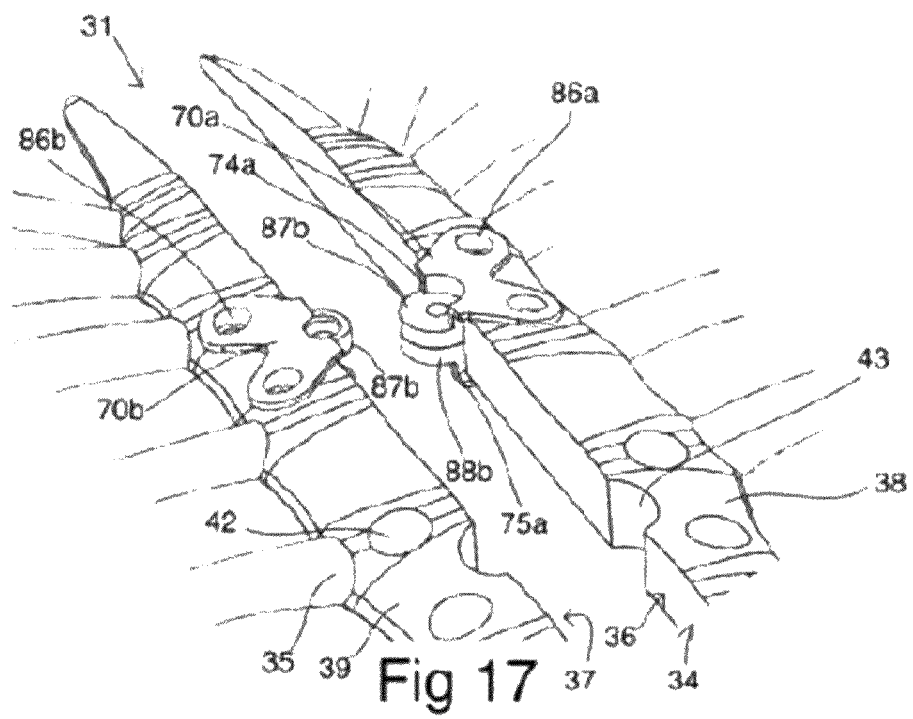
FIG. 17 is a view of a further alternative embodiment of the split sternum prosthesis wherein a bone attachment portion is arranged to a spilt sternum.
Figure 18:
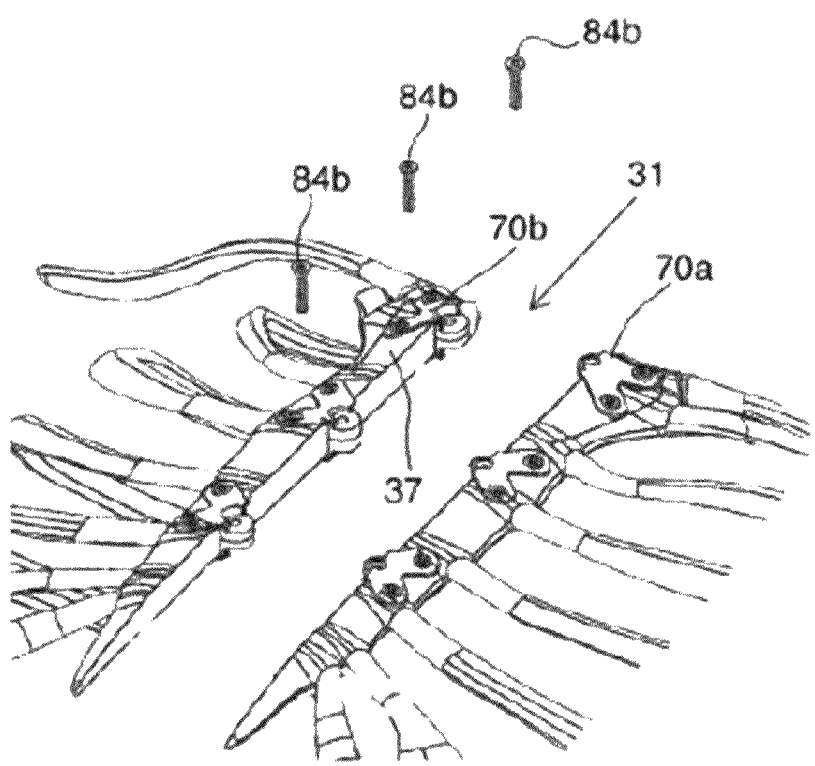
FIG. 18 is a view of a further alternative embodiment of the split sternum prosthesis wherein a three bone attachment portions are arranged to a spilt sternum.

In a further alternative embodiment of the split sternum prosthesis 1, the bone attachment plates 70*a*, 70*b* are divided into two or more bone attachment portions 71*a*, 71*b* that may be arranged along the incision line 31 (see FIGS. 17-20). Each bone attachment plate 70*a*, 70*b* of the bone attachment portions 71*a*, 71*b* has a bone attachment surface 72*a*, 72*b*, 73*a*, 73*b* (FIGS. 20*a* and *b*) and a coupling surface 74*a*, 74*b*, 75*a*, 75*b* (FIG. 19*a*) wherein each bone attachment surface 72*a*, 72*b*, 73*a*, 73*b* is configured to be attached to an incision surface 36, 37 formed along a vertical inline incision 31 after a sternum 30 has been subjected to median sternotomy (FIGS. 17 and 18).

The coupling surfaces 74*a*, 75*a* of the first bone attachment plate 70*a* are configured to be coupled to the coupling surfaces 74*b*, 75*b* of the second bone attachment plate 70*b*.

In this embodiment each bone attachment plate 70*a*, 70*b* has an extension in their longitudinal direction "x" that covers only a part of the length of the sternum bone 30 (see FIG. 17). The coupling surface of the bone attachment plate 70*a*, 70*b* advantageously has a length in the longitudinal direction x from 1.0-4.0 cm, preferably from 1.0-3.0 cm, more preferably from 1.0-2.0 cm. The extension of the bone attachment plate in the transverse extension "y" i.e. the direction substantially perpendicular to the longitudinal direction x corresponds to the tapering width of the sternum half 34, 35 from the incision line 31. The bone attachment plates 70*a*, 70*b* also have an extension in the vertical direction "z" which equals the thickness of the sternum 30, said direction extending from the anterior to the posterior side of the sternum 30.

Each bone attachment plate 70*a*, 70*b* covers only parts of the surface length along the incision line 31 and therefore two or more split sternum prosthesis 1 are advantageously used to pull the two sternum halves 34, 35 together (see FIG. 18). When the cut sternum 30 is fitted with the split sternum prosthesis 1 as disclosed in FIGS. 17-20 the incision 31 of the sternum 30 will eventually grow back together.

Figure 19A:
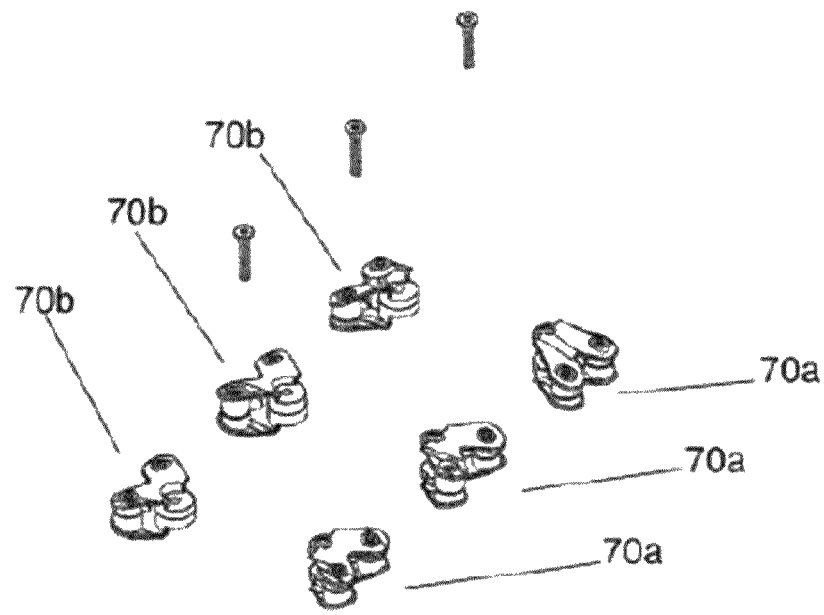
FIG. 19a is a view of the first and second bone attachment plates from FIG. 18
Figure 19B:
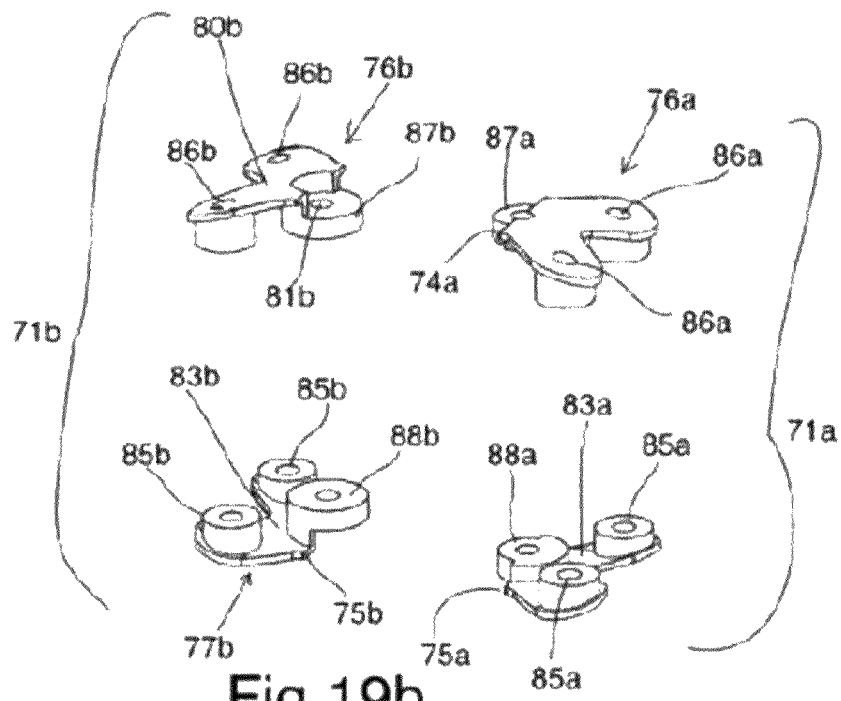
FIG. 19b is an exploded view of one bone attachment portion.
Figure 20A:
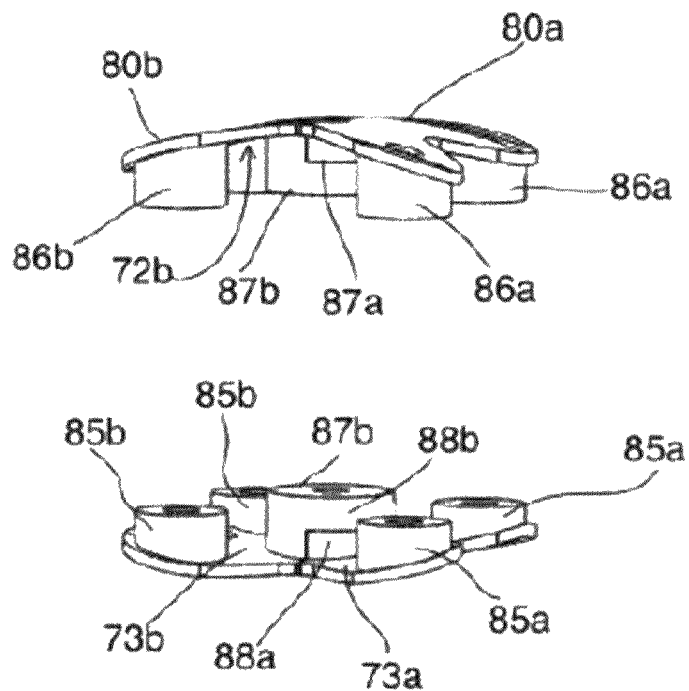
FIG. 20a is a view of a bone attachment portion wherein the anterior sections are connected and the posterior sections are connected.
Figure 20B:
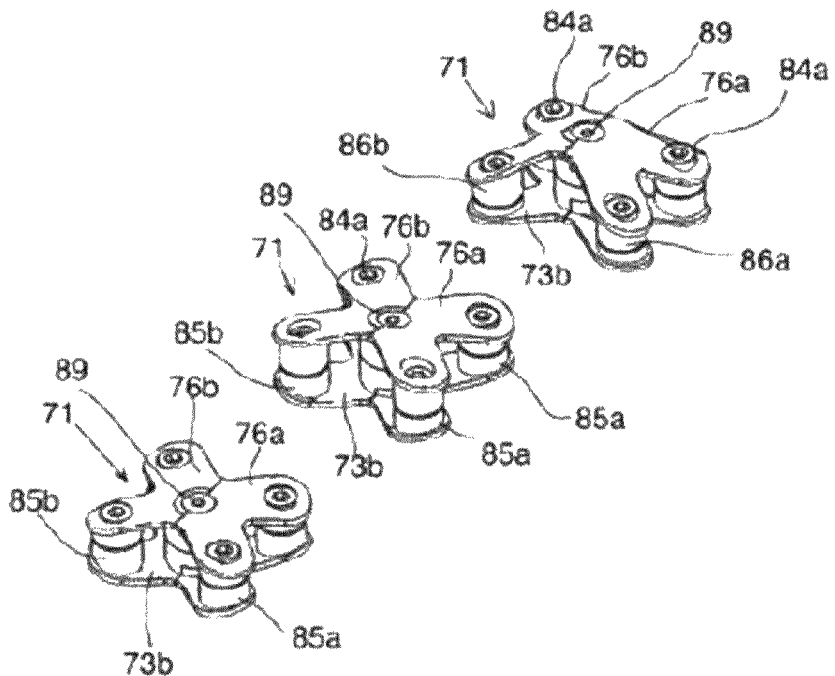
FIG. 20b is a view of the bone attachment portion

Each bone attachment plate 70*a*, 70*b* comprises an anterior section 76*a*, 76*b* and a posterior section 77*a*, 77*b*, wherein each of the anterior and the posterior sections 76*a*, 76*b*, 77*a*, 77*b* have a section fold along their longitudinal extensions x dividing said section into a bone anchoring segment 80*a*, 80*b*, 82*a*, 82*b* having a first planar extension and a coupling segment 81*a*, 81*b*, 83*a*, 83*b* having a second planar extension, the first planar extension being perpendicular to the second planar extension (see FIG. 19*b*).

The bone attachment surfaces 72*a*, 72*b*, 73*a*, 73*b* of the anterior and posterior sections 76*a*, 76*b* 77*a*, 77*b* may be smooth, but preferably they are rough with hills and valleys, and/or covered with netting.

The bone attachment plates 70*a*, 70*b* are attached to the sternum halves 34, 35 by means of bone fastening means selected from the group consisting of bone cement, biocompatible glue, bone fixation screws, connector screws and/or bolts and bolt receiving means. Advantageously the bone fastening means are through bolts 84*a*, 84*b* and bolt receiving means 85*a*, 85*b* See FIG. 20*b*). The bone attachment plates 70*a*, 70*b* are attached to the sternum halves 34, 35 by means of bone fastening means analogous to what was described in connection with FIGS. 5, 6 and 7 above.

The bone attachment plates 70*a*, 70*b* are fastened to the sternum halves by means of bone connecting means such as e.g. through bolts 84*a*, 84*b* fitted into through holes 86*a*, 86*b* provided on the anterior sections 76*a*, 76*b* of the bone attachment plates 70*a*, 70*b* and thereafter pushed through bone through holes 42 provided in the sternum halves 34, 35 and fastened into the bolt receiving means 85*a*, 85*b* provided on the posterior sections 77*a*, 77*b* of the bone attachment plates 70*a*, 70*b*.

Once connected to the two sternum halves 34, 35 the two bone attachment plates 70*a*, 70*b* are coupled together in an analogous manner to what has already described for the prosthesis 1 in connection with FIGS. 5, 6, 8 and 9. In short, the two sternum halves 34, 35 are coupled together by securing the first and second bone attachment plates 70*a*, 70*b* together by means of a closure arrangement, said closure arrangement comprises anterior and posterior connecting means 87*a*, 87*b*, 88*a*, 88*b* arranged on the first and second bone attachment plates 70*a*, 70*b*, said connecting means 87*a*, 87*b*, 88*a*, 88*b* enable said bone attachment plates 70*a*, 70*b* to be pulled together and joined in a tight fit by fastening means 88, 89. For more details see analogous disclosure in connection with FIGS. 5, 6, 8 and 9 above.

The split sternum prosthesis 1 disclosed in FIGS. 17-19 provides an alternative way of closing the chest cavity after a sternotomy procedure. In this embodiment the two sternum halves 34, 35 are aligned and pulled together into a firm and secure connection enabling the sternum bone 30 to heal in a stable manner. The bone attachment plates 70*a*, 70*b* are tightly secured to the sternum halves 34, 35 by means of through bolts 84*a*, 84*b* which are fitted through the sternum and fastened into bolt receiving means 85*a*, 85*b* on the opposite side of the sternum bone 30. Thereafter the bone attachment plates 70*a*, 70*b* are secured to one another by means of the closure arrangement 86*a*, 86, 87*a*, 87*b* and through going closure bolts 89 which are fastened into bolt closure receiving means 88. Said closure arrangement provides a double shear bolt connection wherein the pulling forces from all sections 76*a*, 76*b*, 77*a*, 77*b* are evenly distributed along the through going closure bolt 89.

The invention claimed is:

1. A split sternum prosthesis configured for use after a sternum has been subjected to median sternotomy, during which the sternum is divided into a first and a second sternum half, each sternum half having an anterior surface, a posterior surface and an incision surface; said incision surface extending in a vertical direction z between said anterior surface and said posterior surface; said split sternum prosthesis comprising a first bone attachment plate and a second bone attachment plate, each of the first and second bone attachment plates having a longitudinal extension x configured to correspond to at least part of a length of the sternum, a transverse extension y configured to correspond to at least part of a width of a sternum half, and a vertical extension z configured to correspond to a thickness of the sternum, characterized in that:

the first and the second bone attachment plates each have at least one bone attachment surface, wherein the at least one bone attachment surface of each of the first and second bone attachment plates comprises a first portion that is configured to cover at least a portion of the incision surface of a respective sternum half, a second portion that is configured to cover at least part of the anterior surface of the respective sternum half, and a third portion that is configured to cover at least part of the posterior surface of the respective sternum half; and a coupling surface configured to extend in the vertical direction z between an anterior and a posterior side of the sternum is arranged on each bone attachment plate, on a side opposite to the first portion of the bone attachment surface that is configured to cover at least a portion of said incision surface, wherein said coupling surface of the first bone attachment plate is configured to be coupled to the coupling surface of the second bone attachment plate.

2. The split sternum prosthesis according to claim 1, characterized in that the longitudinal extension x of each of the first and second bone attachment plates is configured to correspond to a full length of the sternum.

3. The split sternum prosthesis according to claim 2, wherein each of the bone attachment plates comprises an anterior section and a posterior section.

4. The split sternum prosthesis according to claim 1, wherein each of the first and second bone attachment plates comprises a respective anterior section and a respective posterior section, wherein the anterior section and the posterior section of each respective bone attachment plate of the first and second bone attachment plates have respective section folds along the longitudinal extension x of the respective bone attachment plate, the section folds of the anterior section and the posterior section of the respective bone attachment plate respectively dividing each of said anterior section and said posterior section into a bone anchoring segment having a first planar extension and a coupling segment having a second planar extension, the first planar extension being perpendicular to the second planar extension, wherein the anterior section of each bone attachment plate of the first and second bone attachment plates defines the second portion of the attachment surface of said bone attachment plate, wherein the posterior section of each bone attachment plate of the first and second bone attachment plates defines the third portion of the attachment surface of said bone attachment plate, and wherein the anterior section and the posterior section of each bone attachment plate of the first and second bone attachment plates cooperate to define the first portion of the attachment surface of said bone attachment plate and the coupling surface of said bone attachment plate.

5. The split sternum prosthesis according to claim 4, characterized in that each of the coupling segments has a coupling segment edge extending in parallel to the section fold, wherein anterior and posterior coupling segment edges of each bone attachment plate are arranged to be coupled together to cover at least part of a first and a second incision surface.

6. The split sternum prosthesis according to claim 4, characterized in that bone attachment surfaces of the anterior and posterior sections are smooth.

7. The split sternum prosthesis according to claim 4, characterized in that bone attachment surfaces of the anterior and posterior sections are rough with hills and valleys, and/or covered with netting.

8. The split sternum prosthesis according to claim 4, wherein each coupling segment of the anterior and the posterior sections defines the first portion of the bone attachment surface on a respective first side of said each coupling segment and the coupling surface on a respective opposing, second side of said each coupling segment.

9. The split sternum prosthesis according to claim 1, characterized in that the first and second bone attachment plates are configured to be attached to the sternum halves by means of bone fastening means selected from the group consisting of bone cement, biocompatible glue, bone fixation screws, connector screws, and bolts with bolt receiving means.

10. The split sternum prosthesis according to claim 9, characterized in that bone fastening means are through bolts with nuts.

11. The split sternum prosthesis according to claim 10, characterized in that said through bolts are fitted into through holes provided on the anterior sections of the bone attachment plates and thereafter pushed through bone through holes provided in the sternum halves and fastened into the bolt receiving means provided on the posterior sections of the bone attachment plates.

12. The split sternum prosthesis according to claim 1, characterized in that the first and second bone attachment plates are configured to couple the two sternum halves together through a closure arrangement that couples the first and second bone attachment plates together.

13. The split sternum prosthesis according to claim 12, characterized in that said closure arrangement comprises anterior and posterior connecting elements arranged on the first and second bone attachment plates, wherein said connecting elements enable said bone attachment plates to be pulled together and joined in a tight fit by one or more fasteners.

14. The split sternum prosthesis according to claim 13, characterized in that said anterior connecting elements comprise second anterior projections protruding in a first lateral direction from the anterior section of the second bone attachment plate across the incision line to at least partly overlap into an anterior section of the first bone attachment plate; and first anterior projections protruding in a second lateral direction opposite from the first lateral direction from the anterior section of the first bone attachment plate and across the incision line to at least partly overlap into the anterior section of the second bone attachment plate; and cut-in portions provided on coupling surfaces of each first and second anterior sections into which the first and second anterior projections protrude.

15. The split sternum prosthesis according to claim 14, characterized in that the first and second anterior projections are lock loops.

16. The split sternum prosthesis according to claim 14, characterized in that said posterior connecting elements comprise
- first posterior projections protruding in a first lateral direction from a posterior section of the first bone attachment plate across the incision line to at least partly overlap into a posterior section of the second bone attachment plate; and
- cut-in portions provided onto coupling surfaces of each first and second posterior sections into which the posterior projection protrudes.

17. The split sternum prosthesis according to claim 16, characterized in that said first posterior projections are lock loops.

18. The split sternum prosthesis according to claim 14, characterized in that said one or more fasteners are closure bolts and bolt closure receiving means.

19. The split sternum prosthesis according to claim 12, wherein the first and second bone attachment plates comprise respective anterior and posterior sections, wherein the anterior section and the posterior section of each respective bone attachment plate of the first and second bone attachment plates cooperate to define the coupling surfaces of the respective bone attachment plate, wherein said first and second bone attachment plates are configured to be coupled together such that said coupling surfaces on the anterior and posterior sections of the first bone attachment plate, are brought into a tight closure with coupling surfaces on the anterior and the posterior sections of the second bone attachment plate.

20. The split sternum prosthesis according to claim 19, characterized in that through going closure bolts are fitted into and pushed through first projections of the second bone attachment plate, through anterior projections of the first bone attachment plate, through posterior lock loops of the first bone attachment plate and thereafter secured into bolt closure receiving means arranged on the first attachment plate.

\* \* \* \* \*